(12) United States Patent
Kim et al.

(10) Patent No.: US 10,006,920 B2
(45) Date of Patent: Jun. 26, 2018

(54) DIAGNOSTIC KIT FOR DIAGNOSIS OF ABNORMAL PROTEIN AGGREGATION- OR MISFOLDING-RELATED DISEASES USING DISSOCIATION OF PROTEIN AGGREGATES

(71) Applicant: KOREA INSTITUTE OF SCIENCE AND TECHNOLOGY, Seoul (KR)

(72) Inventors: Young Soo Kim, Yongin-si (KR); Dong Jin Kim, Seoul (KR); Hye Yun Kim, Seoul (KR); Soo Min Cho, Seoul (KR); Tae Song Kim, Seoul (KR); Hyunjin Kim, Seoul (KR); Sejin Lee, Yeosu-si (KR); Kyoseon Hwang, Seoul (KR); Jee Hoon Roh, Seoul (KR); Jae-Young Koh, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 1 day.

(21) Appl. No.: 14/787,146

(22) PCT Filed: Apr. 25, 2014

(86) PCT No.: PCT/KR2014/003643
§ 371 (c)(1),
(2) Date: Oct. 26, 2015

(87) PCT Pub. No.: WO2014/175693
PCT Pub. Date: Oct. 30, 2014

(65) Prior Publication Data
US 2016/0103139 A1    Apr. 14, 2016

Related U.S. Application Data

(60) Provisional application No. 61/816,343, filed on Apr. 26, 2013.

(30) Foreign Application Priority Data

Apr. 2, 2014 (KR) .......................... 10-2014-0038988
Apr. 2, 2014 (KR) .......................... 10-2014-0038989

(51) Int. Cl.
*G01N 33/68* (2006.01)
*A61K 38/17* (2006.01)
*C07K 14/47* (2006.01)

(52) U.S. Cl.
CPC ..... *G01N 33/6893* (2013.01); *G01N 33/6827* (2013.01); *G01N 33/6896* (2013.01); *A61K 38/1716* (2013.01); *C07K 14/4711* (2013.01); *G01N 2333/4709* (2013.01); *G01N 2800/2821* (2013.01)

(58) Field of Classification Search
None
See application file for complete search history.

(56) References Cited

U.S. PATENT DOCUMENTS

2011/0144111 A1    6/2011 Kim et al.

FOREIGN PATENT DOCUMENTS

| CN | 1809352 A | 7/2006 |
|---|---|---|
| JP | 2005-104975 A | 4/2005 |
| JP | 2007-501277 A | 1/2007 |
| JP | 2008-511291 A | 4/2008 |
| JP | 2008-519988 A | 6/2008 |
| JP | 2009-528380 A | 8/2009 |
| KR | 2011/0066623 A | 6/2011 |
| WO | 00/68694 A1 | 11/2000 |
| WO | 2004/110354 A2 | 12/2004 |
| WO | 2006/036291 A2 | 4/2006 |
| WO | 2006/053251 A2 | 5/2006 |
| WO | 2007/103683 A2 | 9/2007 |
| WO | 2011/064225 A1 | 6/2011 |
| WO | 2011/070174 A1 | 6/2011 |
| WO | 2013/138512 A1 | 9/2013 |

OTHER PUBLICATIONS

Ditto et al. Enrichment and analysis of Alzheimer's Aβ1-42 peptide in human plasma and whole blood. Journal of Neuroscience Methods 182 (2009) 260-265.*
Slemmon et al. Distribution of Abeta peptide in whole blood. J Chromatogr B Analyt Technol Biomed Life Sci. Feb. 1, 2007;846(1-2):24-31. Epub Aug. 30, 2006.*
EPPS compound. Sigma-Aldrich. http://www.sigmaaldrich.com/catalog/product/sigma/e9502?lang=en&region=US downloaded Aug. 30, 2017.*
Hensley et al. A model for beta-amyloid aggregation and neurotoxicity based on free radical generation by the peptide: relevance to Alzheimer disease. Proc Natl Acad Sci U S A. Apr. 12, 1994;91(8):3270-4. (Year: 1994).*
Perrin et al., Multimodal techniques for diagnosis and prognosis of Alzheimer's disease , Nature, Oct. 15, 2009, pp. 916-922, vol. 461.
Oijen et al., Plasma Aβ1-40 and Aβ1-42 and the risk of dementia: a prospective case-cohort study,Jul. 6, 2006, pp. 655-660, vol. 5, Articles.
Mayeux et al., Plasma Aβ40 and Aβ42 and Alzheimer's disease Relation to age, mortality, and risk, Neurology 61 November (1 of 2) 2003, pp. 1185-1190.
Sundelof et al., Plasma β Amyloid and the Risk of Alzheimer Disease and Dementia in Elderly Men A Prospective, Population-Based Cohort Study, Arch Neurol, Feb. 2008, pp. 256-263, vol. 65 (No. 2).
Hansson et al., Evaluation of plasma Aβ40 and Aβ42 as predictors of conversion to Alzheimer's disease in patients with mild cognitive impairment, Neurobiology of Aging 31 (2010) , May 19, 2008, pp. 357-367.
Lopez et al., Plasma amyloid levels and the risk of AD in normal subjects in the Cardiovascular Health Study, Neurology, May 6, 2008. pp. 1-15 70(19): 1664-1671.

* cited by examiner

*Primary Examiner* — Marcela M Cordero Garcia
*Assistant Examiner* — Jia-Hai Lee
(74) *Attorney, Agent, or Firm* — Goldilocks Zone IP Law (57) ABSTRACT

The present disclosure relates to a diagnostic kit capable of accurately diagnosing diseases or disorders related with abnormal aggregation or misfolding of proteins, including disorders or diseases caused by aggregation of β-amyloid such as Alzheimer's disease as well as disorders or diseases caused by aggregation of other proteins, based on concentration analysis of the aggregated proteins before and after dissociation.

5 Claims, 6 Drawing Sheets

DIAGNOSTIC KIT FOR DIAGNOSIS OF ABNORMAL PROTEIN AGGREGATION- OR MISFOLDING-RELATED DISEASES USING DISSOCIATION OF PROTEIN AGGREGATES

TECHNICAL FIELD

The present disclosure relates to a blood diagnostic kit capable of accurately diagnosing diseases or disorders related with abnormal aggregation or misfolding of proteins, including disorders or diseases caused by aggregation of β-amyloid such as Alzheimer's disease as well as disorders or diseases caused by aggregation of other proteins, based on concentration analysis of the aggregated proteins before and after dissociation.

BACKGROUND ART

Neuronal malfunction and damage may be induced by toxic, aggregation-prone proteins and a number of neurological disorders are characterized by such conditions. These include disorders such as amyotrophic lateral sclerosis, Alzheimer's disease, Parkinson's disease, prion disease, polyglutamine expansion disease, spinocerebellar ataxia, spinal and bulbar muscular atrophy, spongiform encephalopathy, tauopathy, Huntington's disease or dystonia.

Toxic, aggregation-prone proteins that cause such diseases and genes encoding the proteins have been identified. Normal metabolic enzymes recycle proteins creating a perpetual cycle of synthesis and degradation. Mutation in these genes results in abnormal accumulation and degradation of misfolded proteins. These misfolded proteins are known to result in neuronal inclusions and plaques which may be indicative of neuronal damage. Therefore, the understanding of cellular mechanisms and the identification of molecular tools required for the reduction, inhibition and amelioration of such misfolded proteins are critical. Furthermore, an understanding of the effects of protein misfolding and aggregation on neuronal survival will allow the development of rational, effective treatment for these disorders.

Alzheimer's disease, the most common form of dementia, is a neurodegenerative disorder caused by damage of neurons and synapses due to abnormal aggregation of β-amyloids and tau proteins that have existed normally in the brain, leading to formation of amyloid plaques (Aβ plaques) and neurofibrillary tangles, respectively.

Alzheimer's disease is the third cause of age-related deaths, followed by cerebrovascular disease and cancer. The disease is known for placing a great burden on caregivers including psychological, economic and social aspects because the mean duration of the disease is over 10 years.

β-Amyloids, specifically found in the brains of Alzheimer patients are peptides generated by metabolism by secretases. They occur as monomers, oligomers, profibrils, fibrils or plaques depending on the progress of the disease. Among them, the oligomers and profibrils exhibiting active dynamic variation are known as the main cause that damages the brain cells.

Clinical trials revealed that abnormal aggregation of β-amyloids occurs in the brain 10-15 years prior to the onset of the symptoms of Alzheimer's disease (Perrin R J, Fagan A M, Holtzman D M. "Multimodal techniques for diagnosis and prognosis of Alzheimer's disease." Nature. 2009; 461: 916-22). Since the β-amyloid can be transported across the blood-brain barrier (BBB) by RAGEs and LRPs present in the BBB, in the form of small monomers, dimers or trimers, the change in β-amyloid concentration in blood may be directly associated with the progress of Alzheimer's disease.

There are opposing opinions about diagnosis of Alzheimer's disease based on the β-amyloid concentration in blood. There are reports that β-amyloid is increased with the progress of Alzheimer's disease (van Oijen M, Hofman A, Soares H D, Koudstaal P J, Breteler M M. "Plasma Abeta (1-40) and Abeta(1-42) and the risk of dementia: a prospective case-cohort study." Lancet Neurol. 2006; 8:655-660, Mayeux R, Honig L S, Tang M X, Manly J, Stern Y, Schupf N, Mehta P D. "Plasma A[beta]40 and A[beta]42 and Alzheimer's disease: relation to age, mortality, and risk." Neurology. 2003; 8: 1185-1190), whereas there are opposing reports that β-amyloid in blood decreases with the progress of Alzheimer's disease (Sundstrom J, Ingelsson E, Ronnemaa E, Arnlov J, Gunnarsson M D, Hyman B T, Basun H. et al. "Plasma beta amyloid and the risk of Alzheimer disease and dementia in elderly men: a prospective, population-based cohort study." Arch Neurol. 2008; 8: 256-263). Furthermore, there are reports that the change in β-amyloid in blood is unrelated with the decline in cognitive ability due to Alzheimer's disease (Hansson O, Zetterberg H, Vanmechelen E, Vanderstichele H, Andreasson U, Londos E, Wallin A, Minthon L, Blennow K. "Evaluation of plasma Abeta(40) and Abeta(42) as predictors of conversion to Alzheimer's disease in patients with mild cognitive impairment." Neurobiol Aging. 2010; 8: 357-367, Lopez O L, Kuller L H, Mehta P D, Becker J T, Gach H M, Sweet R A, Chang Y F, Tracy R, DeKosky S T. "Plasma amyloid levels and the risk of AD in normal subjects in the cardiovascular health study." Neurology. 2008; 8: 1664-1671). The discrepancies in study results seem to be caused by the fact that it is difficult to accurately determine the level of β-amyloids in blood.

At present, a definitive diagnosis of Alzheimer's disease can be made only through autopsy after death. Although its progress can be diagnosed by indirect examination of symptoms based on physical, neurological or physiological examination, measurement of β-amyloid in the cerebrospinal fluid and, most accurately, monitoring of structural and functional change of the brain and identification of β-amyloid plaques through brain imaging, they are very invasive and cost a lot. Because of these disadvantages, it is difficult to accurately diagnose Alzheimer's disease.

DISCLOSURE

Technical Problem

The present disclosure is directed to providing a blood diagnostic kit capable of accurately diagnosing diseases or disorders related with abnormal aggregation or misfolding of proteins, including disorders or diseases caused by aggregation of β-amyloid such as Alzheimer's disease as well as disorders or diseases caused by aggregation of other proteins, based on concentration analysis of the aggregated proteins before and after dissociation.

Technical Solution

In an aspect, the present disclosure provides a blood diagnostic kit for diagnosing diseases or disorders related with abnormal aggregation or misfolding of proteins, which measures the concentration of proteins in plasma before and after administering a protein monomerizing composition.

Specifically, the diagnostic kit for diagnosing diseases or disorders related with abnormal aggregation or misfolding of proteins according to the present disclosure may include: (a) a detection unit 1 measuring the concentration of proteins in plasma before administering a composition for monomerizing abnormally aggregated or misfolded proteins in vivo; (b) a detection unit 2 measuring the concentration of proteins in plasma after administering the protein monomerizing composition; and (c) a calculation unit calculating the difference of the concentration measured by the detection unit 1 and the concentration measured by the detection unit 2 using [Equation 1]:

Concentration of proteins in plasma after administering protein monomerizing composition (B)–Concentration of proteins in plasma before administering protein monomerizing composition (A).   [Equation 1]

The detection unit 2 may measure the concentration of proteins in plasma 20-450 hours after the administering of the protein monomerizing composition.

The protein may be β-amyloid.

The proteins in plasma after administering the protein monomerizing composition may be ones that have been formed from dissociation of β-amyloid oligomers, profibrils, fibrils and plaques in the brain and have transported into blood.

The diagnostic kit for diagnosing diseases or disorders related with abnormal aggregation or misfolding of proteins may diagnose as diseases or disorders related with abnormal aggregation or misfolding of proteins if the value calculated by the calculation unit is a positive (+) value.

The protein monomerizing composition may contain EPPS, 4-(2-Hydroxyethyl)-1-piperazinepropanesulfonic acid represented by Chemical Formula 1 as an active ingredient:

Chemical Formula 1

The protein monomerizing composition may dissociate β-amyloid oligomers, profibrils, fibrils and plaques into monomers.

In another aspect, the present disclosure provides a diagnostic kit for diagnosing diseases or disorders related with abnormal aggregation or misfolding of proteins based on decrease of protein monomer concentration in whole blood, which measures protein monomer concentration in plasma without treating with a protein monomerizing composition, protein monomer concentration in plasma after treating with the protein monomerizing composition and protein monomer concentration in whole blood after treating with the protein monomerizing composition.

Specifically, the diagnostic kit for diagnosing diseases or disorders related with abnormal aggregation or misfolding of proteins may include: (A) a detection unit 1' measuring protein monomer concentration in plasma not treated with a protein monomerizing composition; (B) a detection unit 2' measuring protein monomer concentration in plasma treated with the protein monomerizing composition; (C) a detection unit 3' measuring protein monomer concentration in whole blood treated with the protein monomerizing composition; and (D) a calculation unit calculating the ratio of the concentration measured by the detection unit 2' and the concentration measured by the detection unit 3' using [Equation 2] or calculating the ratio of the concentration measured by the detection unit 1' and the concentration measured by the detection unit 2' using [Equation 3]:

Protein monomer concentration in whole blood treated with protein monomerizing composition/Protein monomer concentration in plasma treated with protein monomerizing composition   [Equation 2]

Protein monomer concentration in plasma not treated with protein monomerizing composition/Protein monomer concentration in plasma treated with protein monomerizing composition.   [Equation 3]

The detection unit 1' may measure the concentration of proteins in plasma separated from whole blood without treating with a monomerizing composition or 23-25 hours after treating with a vehicle.

The detection unit 2' and the detection unit 3' may measure the concentration of proteins 23-25 hours after treating with the protein monomerizing composition.

The protein may be β-amyloid.

The monomerized protein may be one that has been formed from dissociation of β-amyloid dimers, oligomers, profibrils, fibrils and plaques, β-amyloid 40/42 aggregates, β-amyloid monomers bound to other proteins, β-amyloid aggregates bound to other proteins, β-amyloid bound to fats, β-amyloid bound to carbohydrates, β-amyloid bound to nucleic acids and β-amyloid monomers bound to blood cells.

The diagnostic kit for diagnosing diseases or disorders related with abnormal aggregation or misfolding of proteins may diagnose as diseases or disorders related with abnormal aggregation or misfolding of proteins if the value calculated by the calculation unit is smaller than 1.0.

The vehicle may be phosphate-buffered saline (PBS).

The protein monomerizing composition may contain EPPS represented by [Chemical Formula 1] as an active ingredient.

Advantageous Effects

A diagnostic kit for diagnosing diseases or disorders related with abnormal aggregation or misfolding of proteins according to the present disclosure can diagnose and predict diseases or disorders related with abnormal aggregation or misfolding of proteins, including disorders or diseases caused by aggregation of β-amyloid such as Alzheimer's disease as well as disorders or diseases caused by aggregation of other proteins, by measuring the protein concentration before and after administering a protein monomerizing composition using detection units 1 and 2, particularly by indirectly measuring the concentration of protein aggregates in plasma by dissociating them.

Another diagnostic kit for diagnosing diseases or disorders related with abnormal aggregation or misfolding of proteins according to the present disclosure can diagnose and predict diseases or disorders related with abnormal aggregation or misfolding of proteins, including disorders or diseases caused by aggregation of β-amyloid such as Alzheimer's disease as well as disorders or diseases caused by aggregation of other proteins, by measuring the concentration of proteins in plasma and whole blood using the detection units 1 and 2, based on the fact that the protein concentration decreases in whole blood as monomerized proteins are removed, aggregated proteins are dissociated into monomers or multimers with small molecular weights in whole blood and plasma, leading to increased protein concentration, and the proteins bound to other proteins, fats, carbohydrates, nucleic acids and blood cells are also dissociated in whole blood and plasma.

The currently available methods for diagnosing diseases or disorders related with abnormal aggregation or misfolding of proteins are invasive and applicable only when the diseases or disorders have proceeded to certain stages. Since the aggregation of proteins occurs long before the symptoms of the diseases or disorders related with abnormal aggregation or misfolding of proteins are observed, it is not easy to achieve the effect of drugs designed to inhibit protein aggregation. Therefore, it is necessary to detect protein aggregation in the brain before the symptoms occur. Accordingly, the diagnostic kit for diagnosing diseases or disorders related with abnormal aggregation or misfolding of proteins according to the present disclosure, which is less invasive and uses common diagnostic samples such as plasma, serum or blood, will be very useful since it allows accurate diagnosis of the diseases or disorders related with abnormal aggregation or misfolding of proteins.

BEST MODE

The present disclosure relates to a diagnostic kit capable of accurately diagnosing diseases or disorders related with abnormal aggregation or misfolding of proteins, including disorders or diseases caused by aggregation of β-amyloid such as Alzheimer's disease as well as disorders or diseases caused by aggregation of other proteins, based on concentration analysis of the aggregated proteins before and after dissociation.

The diseases or disorders related with abnormal aggregation or misfolding of proteins may be selected from a group consisting of Parkinson's disease, Huntington's disease, amyotrophic lateral sclerosis, polyglutamine expansion disease, spinocerebellar ataxia, spinal and bulbar muscular atrophy, tauopathy, dystonia, serpin deficiency, cirrhosis, type 2 diabetes, primary systemic amyloidosis, secondary systemic amyloidosis, frontotemporal dementia, senile systemic amyloidosis, familial amyloid polyneuropathy, hereditary cerebral amyloid angiopathy, hemodialysis-associated amyloidosis, age-related macular degeneration, Alzheimer's disease, radiotherapy-induced dementia, axon injury, acute cortical spreading depression, α-synucleinopathy, brain ischemia, permanent focal cerebral ischemia, peripheral nerve regeneration, post-status epilepticus model, spinal cord injury, sporadic amyotrophic lateral sclerosis and a prion disease such as Creutzfeldt-Jakob disease, spongiform encephalopathy and transmissible spongiform encephalopathy.

Correct folding requires proteins to assume one particular structure from a constellation of possible but incorrect conformations. The failure of polypeptides to adopt their proper structure is a major threat to cell function and viability. Misfolded proteins may be toxic in and of themselves and may form aggregates that may have very serious or even lethal consequences. Consequently, elaborate systems have evolved to protect cells from the deleterious effects of misfolded proteins.

In the present disclosure, "protein aggregation" includes the phenomenon of at least two polypeptides contacting each other in a manner that causes either one of the polypeptides to be in a state of desolvation. This may also include a loss of the polypeptide's native function or activity.

In the present disclosure, the "protein" may be specifically β-amyloid.

Hereinafter, the present disclosure is described in more detail.

1. Diagnostic Kit Measuring Concentration of Aggregated Proteins Before and after Dissociation A diagnostic kit of the present disclosure diagnoses diseases or disorders related with abnormal aggregation or misfolding of proteins by measuring the concentration of proteins in plasma before and after administering a protein monomerizing composition.

Specifically, the diagnostic kit according to the present disclosure includes: (a) a detection unit 1 measuring the concentration of proteins in plasma before administering a composition for monomerizing abnormally aggregated or misfolded proteins in vivo; (b) a detection unit 2 measuring the concentration of proteins in plasma after administering the protein monomerizing composition; and (c) a calculation unit calculating the difference of the concentration measured by the detection unit 1 and the concentration measured by the detection unit 2 using [Equation 1]

The detection unit 1 measures the concentration of proteins in plasma before administering a protein monomerizing composition (A).

And, the detection unit 2 measures the concentration of proteins in plasma after orally or parenterally administering the protein monomerizing composition (B). The time at which the measurement is made after administering the protein monomerizing composition is not particularly limited. The measurement may be made specifically 20-450 hours, more specifically 20-300 hours, after the administration.

The calculation unit calculates the difference of the concentration measured by the detection unit 1 (A) and the concentration measured by the detection unit 2 (B) using [Equation 1].

Concentration of proteins in plasma after administering protein monomerizing composition (B)− Concentration of proteins in plasma before administering protein monomerizing composition (A)  [Equation 1]

Figure 1:
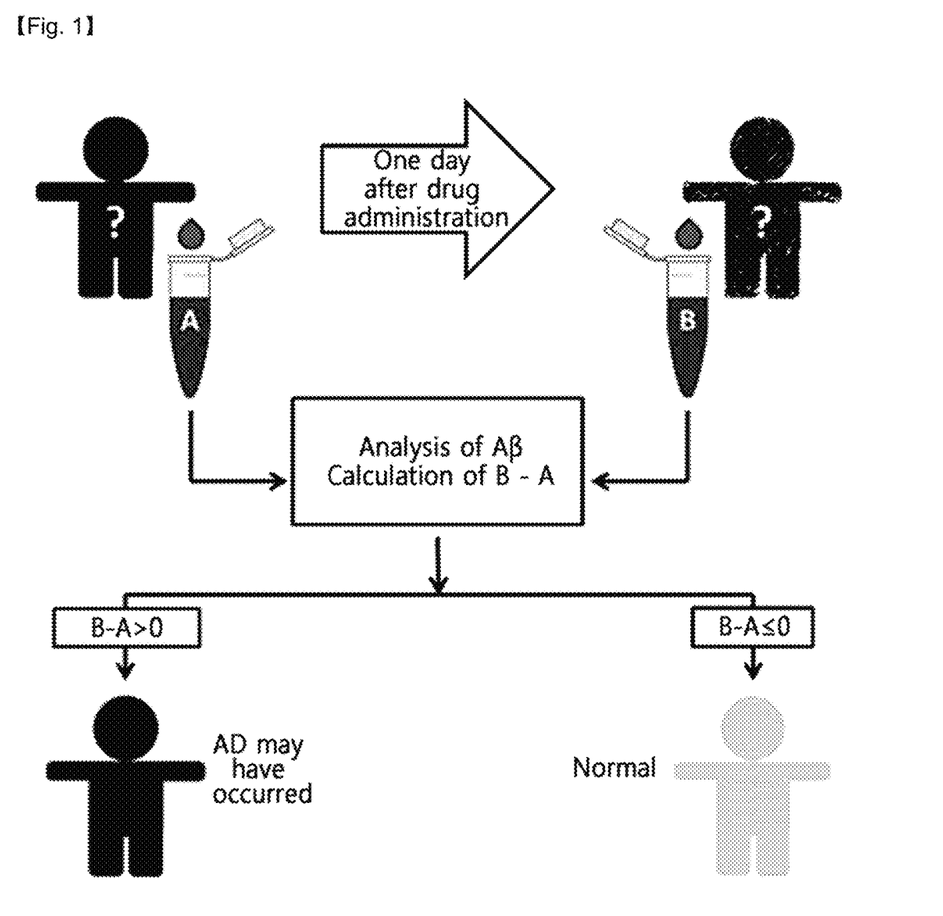
FIG. 1 shows how to diagnose diseases or disorders related with abnormal aggregation or misfolding of proteins by measuring the concentration of proteins in plasma before and after administering a protein monomerizing composition using detection units 1 and 2 according to an exemplary embodiment of the present disclosure.

As seen from FIG. 1, the value calculated using [Equation 1] may be a positive (+) value or negative (−) value. If the value calculated using [Equation 1] is 0 or a negative (−)

value, it may be diagnosed as a normal state wherein diseases or disorders related with abnormal aggregation or misfolding of proteins do not proceed. And, if the value is a positive (+) value, it may be diagnosed as a state wherein the risk of onset of diseases or disorders related with abnormal aggregation or misfolding of proteins is high.

If the value calculated using [Equation 1] is a positive (+) value, it means that the amount of proteins has increased after the administering of the protein monomerizing composition. Since it indicates the progress of protein accumulation in the brain, it may be diagnosed as a state wherein the risk of onset of diseases or disorders related with abnormal aggregation or misfolding of proteins is high.

Figure 2:
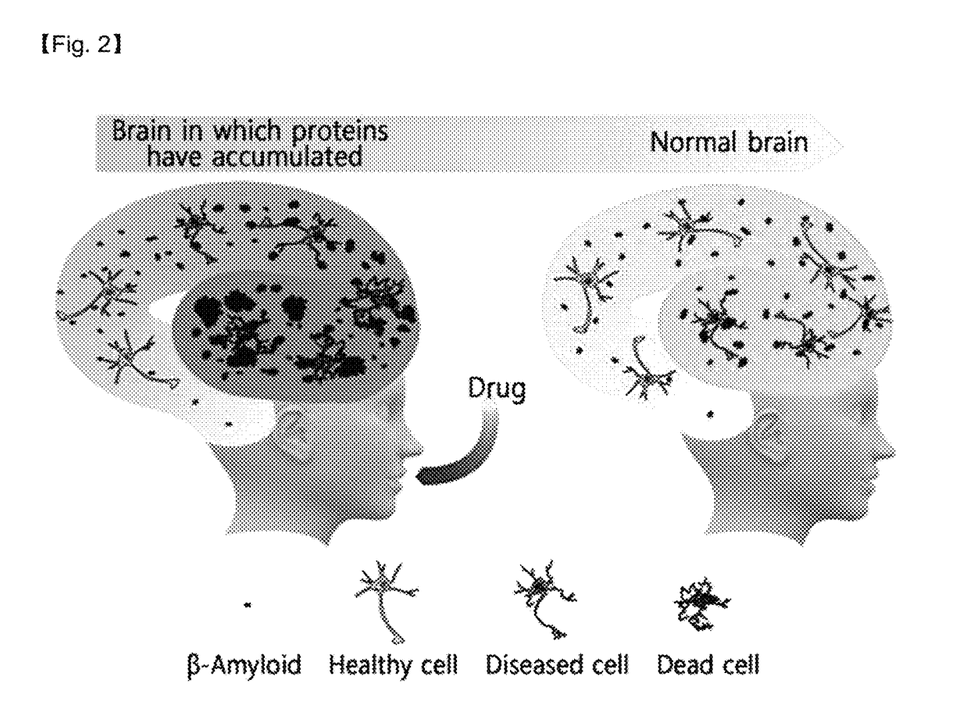
FIG. 2 shows a normal brain and a brain in which proteins have accumulated due to diseases or disorders related with abnormal aggregation or misfolding of proteins.

The principle by which the risk of onset of diseases or disorders related with abnormal aggregation or misfolding of proteins is diagnosed or predicted based on the concentration of proteins in plasma before and after administering the protein monomerizing composition is as follows. In a normal brain, proteins exist as monomers (FIG. 2, right side). Abnormal aggregation of proteins (oligomers, fibrils, plaques, etc.) occurs in the brain (FIG. 2, left side) from 10-15 years before the symptoms of diseases or disorders related with abnormal aggregation or misfolding of proteins occur. If the protein monomerizing composition is administered, the protein concentration in plasma does not increase in the normal brain, since there are no protein oligomers that can be dissociated into monomers in the brain. In contrast, in case of diseases or disorders related with abnormal aggregation or misfolding of proteins, the protein concentration in plasma increases as protein oligomers are dissociated in the brain.

Since the concentration of proteins in the brain cannot be measured directly, it is indirectly measured in plasma in consideration of the fact that protein monomers or multimers with small molecular weights such as dimers, trimers, etc. present in the brain are transported between the brain, cerebrospinal fluid and blood by RAGEs and LRPs existing in the blood-brain barrier (BBB).

Therefore, the proteins existing in plasma after the administering of the protein monomerizing composition may have been formed from dissociation of β-amyloid oligomers, profibrils, fibrils and plaques in the brain. For example, the proteins existing in plasma after the administering of the protein monomerizing composition may be monomers and/or multimers with small molecular weights such as dimers, trimers, etc. which may have been transported by RAGEs and LRPs existing in the BBB.

Since the amount of protein aggregates in blood decreases gradually after a predetermined time has passed since the administering of the protein monomerizing composition, the decrease in protein aggregates in the brain or body may be monitored with the diagnostic kit of the present disclosure.

The protein monomerizing composition may be a composition containing EPPS represented by [Chemical Formula 1] as an active ingredient. However, the protein monomerizing composition is not particularly limited thereto as long as it can dissociate protein oligomers into monomers. The same result as when EPPS is used can be achieved using other substances that can dissociate protein oligomers into monomers.

[Chemical Formula 1]

From SDS-PAGE analysis, it can be seen that the EPPS represented by [Chemical Formula 1] has the activity of dissociating β-amyloid oligomers, profibrils, fibrils and plaque aggregates since the bands of the Aβ 40 and Aβ 42 monomers with sizes of 4.3-4.5 kD appear. Also, electron microscopic observation confirms the activity of dissociating the β-amyloid oligomers, profibrils, fibrils and plaques since no β-amyloid aggregates are observed.

When the composition is used as medicine, the protein monomerizing composition containing the EPPS represented by [Chemical Formula 1] as an active ingredient may be prepared into various formulations for oral or parenteral administration for clinical purposes, although not being limited to.

Formulations for oral administration include, for example, tablets, pills, hard/soft capsules, liquids, suspensions, emulsions, syrups, granules, elixirs, etc. These formulations may further contain, in addition to the active ingredient, a diluent (e.g., lactose, dextrose, sucrose, mannitol, sorbitol, cellulose and/or glycine), a lubricant (e.g., silica, talc, stearic acid and magnesium or calcium salts thereof and/or polyethylene glycol). A tablet may also contain a binder such as magnesium aluminum silicate, starch paste, gelatin, methyl cellulose, sodium carboxymethyl cellulose and/or polyvinylpyrrolidine and, if necessary, it may further contain a disintegrant such as starch, agar, alginic acid or a sodium salt thereof, an effervescent mixture and/or absorbent, a colorant, a flavoring agent and a sweetener.

The protein monomerizing composition containing the EPPS represented by [Chemical Formula 1] as an active ingredient may be administered parenterally. The parenteral administration may be achieved by subcutaneous, intravenous, intramuscular or intrathoracic injection. In order to prepare formulations for parenteral administration, the EPPS represented by [Chemical Formula 1] may be mixed with a stabilizer or a buffer in water to prepare solutions or suspensions, which may be formulated into a unit dosage form in ampoules or vials.

The composition may be sterilized and/or may contain an adjuvant such as a preservative, a stabilizer, a wetting or emulsifying agent, a salt for regulating osmotic pressure, a buffer, etc. and other therapeutically useful substances. The composition may be prepared according to commonly employed mixing, granulating or coating methods.

When the protein monomerizing composition containing the EPPS represented by [Chemical Formula 1] as an active ingredient is formulated into a unit dosage form, it may contain specifically about 0.1-1,500 mg/kg of the EPPS represented by [Chemical Formula 1] as an active ingredient. The administration dose should follow a doctor's prescription depending on factors such as the body weight and age of a patient and particular characteristics and severity of a disease or a disorder. The dose required for treatment of an adult patient is usually in the range of about 0.1-1,000 mg/kg/day, depending on the frequency and intensity of administration. When administering by intramuscular or intravenous administration into an adult, a dose of about 0.5-300 mg/kg/day may be sufficient. But, a larger daily dose may be preferred for some patients.

2. Diagnostic Kit Measuring Dissociation Concentration of Aggregated Proteins in Blood Proteins in blood are the most likely to enter the brain when they are present as monomers and it is expected that it will be almost impossible for aggregates to enter the blood. However, even when proteins enter the blood in the form of monomers, they may aggregate in the blood. In addition, they may also bind to other proteins in the blood.

Therefore, it is impossible to accurately measure the protein monomer concentration in blood simply by measuring the concentration of protein monomers in plasma.

This makes it difficult to distinguish a patient from a healthy person simply by comparing the concentration of protein monomers in plasma. This problem can be solved if the proteins present in blood can be dissociated into monomers and the protein monomer concentration can be accurately measured after separating the protein monomers from other proteins, blood cells, etc. But, there is a report that the stability of protein monomers in whole blood decreases as compared to in plasma (Slemmon J R, Painter C L, Nadanaciva S, Catana F, Cook A, Motter R, Seubert P. "Distribution of Abeta peptide in whole blood." *J Chromatogr B Analyt Technol Biomed Life Sci.* 2007; 846(1-2): 24-31), which may be because the protein monomers are metabolized or engulfed by blood cell components. Accordingly, diseases or disorders related with abnormal aggregation or misfolding of proteins may be accurately diagnosed or predicted by comparing the protein monomer concentration in whole blood with the protein monomer concentration in plasma.

The other proteins may be at least one selected from a group consisting of lactoferrin, clusterin, $\alpha_1$-antitrypsin, apolipoprotein A-IV, apolipoprotein E and apolipoprotein A-I.

Figure 4:
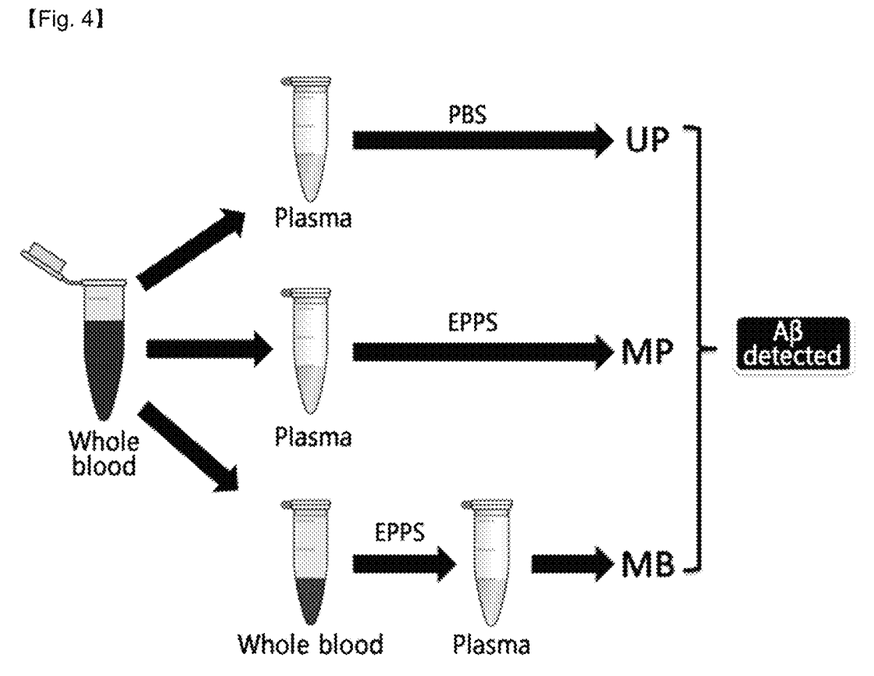
FIG. 4 shows how to diagnose diseases or disorders related with abnormal aggregation or misfolding of proteins by measuring protein monomer concentration in plasma and whole blood treated with a protein monomerizing composition using detection units 1', 2' and 3' according to another exemplary embodiment of the present disclosure.

FIG. 4 shows how to diagnose diseases or disorders related with abnormal aggregation or misfolding of proteins by measuring the protein monomer concentration in plasma and whole blood treated with a protein monomerizing composition using detection units 1', 2' and 3' according to another exemplary embodiment of the present disclosure.

Specifically, a diagnostic kit for diagnosing diseases or disorders related with abnormal aggregation or misfolding of proteins according to the present disclosure includes: (A) a detection unit 1' measuring protein monomer concentration in plasma not treated with a protein monomerizing composition; (B) a detection unit 2' measuring protein monomer concentration in plasma treated with the protein monomerizing composition; (C) a detection unit 3' measuring protein monomer concentration in whole blood treated with the protein monomerizing composition; and (D) a calculation unit calculating the ratio of the concentration measured by the detection unit 2' and the concentration measured by the detection unit 3' using [Equation 2] or calculating the ratio of the concentration measured by the detection unit 1' and the concentration measured by the detection unit 2' using [Equation 3].

The detection unit 1' measures the concentration of proteins in plasma separated from whole blood without treating with a monomerizing composition or 23-25 hours after treating with a vehicle.

The detection unit 2' measures the concentration of proteins in plasma separated from whole blood 23-25 hours after treating with the protein monomerizing composition.

And, the detection unit 3' measures the concentration of proteins in whole blood 23-25 hours after treating with the protein monomerizing composition.

The calculation unit calculates the ratio of the concentration measured by the detection unit 2' and the concentration measured by the detection unit 3' using [Equation 2] or calculating the ratio of the concentration measured by the detection unit 1' and the concentration measured by the detection unit 2' using [Equation 3].

Protein monomer concentration in whole blood
treated with protein monomerizing composition
(MB)/Protein monomer concentration in plasma
treated with protein monomerizing composition
(MP)      [Equation 2]

The value MB/MP calculated using [Equation 2] may satisfy either MB/MP<1.0 or MB/MP≥1.0. If MB/MP<1.0, it may be diagnosed as a state wherein the risk of onset of diseases or disorders related with abnormal aggregation or misfolding of proteins is high. And, if MB/MP≥1.0, it may be diagnosed as a state wherein the risk of onset of diseases or disorders related with abnormal aggregation or misfolding of proteins is low or as a normal state wherein diseases or disorders related with abnormal aggregation or misfolding of proteins do not proceed.

If MB/MP<1.0, it means that the difference in the protein monomer concentration in plasma (MP) and the protein monomer concentration in whole blood (MB), i.e., MP–MB, is large. Since it indicates the concentration of protein aggregates is high, it may be diagnosed as a state wherein the risk of onset of diseases or disorders related with abnormal aggregation or misfolding of proteins is high.

If the plasma wherein protein aggregates and protein monomers are present is treated with the protein monomerizing composition, the protein aggregates are dissociated into monomers, resulting in increase of the protein monomer concentration in plasma (MP). And, since the protein monomers are engulfed or metabolized by blood cells, other proteins, etc. in the whole blood, the protein monomer concentration in whole blood (MB) decreases. Therefore, the difference in MP and MB, i.e., MP–MB, is equal to the concentration of the aggregates. Meanwhile, the amount of proteins in blood and, hence the relative amount of aggregates, are larger as the risk of onset of diseases or disorders related with abnormal aggregation or misfolding of proteins is higher. As a result, since the protein monomer concentration in plasma (MP) increases and the protein monomer concentration in whole blood (MB) decreases due to metabolism and engulfment, MP–MB becomes larger and MB/MP becomes smaller than 1.0.

Protein monomer concentration in plasma not treated
with protein monomerizing composition (UP)/
Protein monomer concentration in plasma
treated with protein monomerizing composition
(MP)      [Equation 3]

The value UP/MP calculated using [Equation 3] may satisfy either UP/MP<1.0 or UP/MP≥1.0. If UP/MP<1.0, it may be diagnosed as a state wherein the risk of onset of diseases or disorders related with abnormal aggregation or misfolding of proteins is high. And, if UP/MP≥1.0, it may be diagnosed as a state wherein the risk of onset of diseases or disorders related with abnormal aggregation or misfolding of proteins is low or as a normal state wherein diseases or disorders related with abnormal aggregation or misfolding of proteins do not proceed.

If UP/MP<1.0, it means that the difference in the concentration of proteins in plasma after treating with the monomerizing composition (MP) and the concentration of proteins in plasma not treated with the protein monomerizing composition (UP), i.e., MP–UP, is large. Since it indicates the concentration of protein aggregates is high, it may be diagnosed as a state wherein the risk of onset of diseases or disorders related with abnormal aggregation or misfolding of proteins is high.

If the plasma wherein protein aggregates and protein monomers are present is treated with the protein monomerizing composition, the protein aggregates are dissociated into monomers, resulting in increase of the protein monomer concentration in plasma (MP). Therefore, the difference in MP and UP, i.e., MP–UP, is equal to the concentration of the aggregates. Meanwhile, the amount of proteins in blood and, hence the relative amount of aggregates, are larger as the risk of onset of diseases or disorders related with abnormal aggregation or misfolding of proteins is higher. As a result, since the protein monomer concentration in plasma (MP) increases, MP–UP becomes larger and UP/MP becomes smaller than 1.0.

The monomerized proteins detected by the detection unit 1', the detection unit 2' and the detection unit 3' are those that have been formed from dissociation of β-amyloid dimers, oligomers, profibrils, fibrils and plaques, β-amyloid 40/42 aggregates, β-amyloid monomers bound to other proteins, β-amyloid bound to fats, β-amyloid bound to carbohydrates, β-amyloid bound to nucleic acids and β-amyloid monomers bound to blood cells.

The protein monomerizing composition may be a composition containing EPPS represented by [Chemical Formula 1] as an active ingredient. However, the protein monomerizing composition is not particularly limited thereto as long as it can dissociate protein oligomers into monomers. It is expected that the same result as when EPPS is used can be achieved using other substances that can dissociate protein oligomers into monomers.

From SDS-PAGE analysis, it can be seen that the EPPS represented by [Chemical Formula 1] has the activity of dissociating β-amyloid dimer, oligomer, profibril, fibril and plaque aggregates, β-amyloid 40/42 aggregates, β-amyloid monomers bound to other proteins and β-amyloid monomers bound to blood cells since the bands of the Aβ 40 and Aβ 42 monomers with sizes of 4.3-4.5 kD appear. Also, electron microscopic observation confirms the activity of dissociating β-amyloid dimers, oligomers, profibrils, fibrils and plaques, β-amyloid 40/42 aggregates, β-amyloid monomers bound to other proteins, β-amyloid bound to fats, β-amyloid bound to carbohydrates, β-amyloid bound to nucleic acids and β-amyloid monomers bound to blood cells.

MODE FOR INVENTION

Hereinafter, the present disclosure will be described in detail through examples. However, it will be apparent to those of ordinary skill in the art that various changes and modifications can be made thereto within the scope and technical spirit of the present disclosure and that such changes and modifications belong to the attached claims.

<Example 1> Diagnostic Kit Measuring Concentration of Aggregated Proteins Before and after Dissociation 1. Preparation of Mouse Female APP/PS1 transgenic mice were used as test animals. A total of 32 mice were used (eleven 5-6 month-olds and twenty-one 7.2-8.6 and 13 month-olds). 5-6-month-old mice were used since β-amyloid plaque accumulation in the brain begins from 5 months.

The transgenic APP/PS1 mouse model was B6C3-Tg (APPswe, PSEN1dE9)85Dbo/Mmjax purchased from the Jackson Laboratory (USA) and maintained and used for experiments under the guideline of the Animal Care and Use Committee.

EPPS was administered to each of the 32 mice at a dose of 1,000 mg/kg/day.

2. Blood Drawing and Measurement of β-Amyloid Concentration

Blood was drawn from the of the retro-orbital venous plexus of the mouse using a microtube (Marienfeld, Germany) treated with 80 IU/mL heparin before and after the administration of EPPS. The blood drawing after the administration of EPPS was performed 1 day, 5 days, 19 days and 33 days after the administration of EPPS.

The blood was collected in an Eppendorf tube and centrifuged at 13,500 rpm and 4° C. for 5 minutes. Plasma separated from the cell fraction was collected in an Eppendorf tube for immediate use or for storage at −80° C. for later use.

β-Amyloid concentration in the plasma collected before and after the administration of EPPS was measured by detection units 1 and 2 of a kit. B−A was calculated by a calculation unit from the measured concentrations using [Equation 1]. Average of three measurements is shown in Tables 1-5.

TABLE 1

| | Young (5-6 months) | | | | | | | | | | |
|---|---|---|---|---|---|---|---|---|---|---|---|
| | 1 | 2 | 3 | 4 | 5 | 6 | 7 | 8 | 9 | 10 | 11 |
| B-A (1 day) | 52.151 | 20.430 | 191.398 | 124.731 | 108.065 | 102.326 | 89.535 | 94.186 | 146.802 | 22.674 | 98.547 |

TABLE 2

| | Aged (7.2 months or older) | | | | | | | | | | |
|---|---|---|---|---|---|---|---|---|---|---|---|
| | 1 | 2 | 3 | 4 | 5 | 6 | 7 | 8 | 9 | 10 | 11 |
| B-A (1 day) | 78.802 | 12.442 | 15.385 | 7.373 | 182.867 | 10.138 | 13.364 | 7.373 | 11.060 | 41.434 | 20.276 |
| | 12 | 13 | 14 | 15 | 16 | 17 | 18 | 19 | 20 | 21 | |
| B-A (1 day) | 4.147 | 16.129 | 194.580 | 18.894 | 6.119 | 345.979 | 19.816 | 156.294 | 180.594 | 140.559 | |

TABLE 3

| | Aged (7.2 months or older) | | | | | | | | | | |
|---|---|---|---|---|---|---|---|---|---|---|---|
| | 1 | 2 | 3 | 4 | 5 | 6 | 7 | 8 | 9 | 10 | 11 |
| B-A (5 days) | 93.531 | 76.049 | 170.979 | 86.122 | 108.916 | 311.820 | 134.965 | 170.656 | 207.692 | 163.986 | 51.584 |
| | 12 | 13 | 14 | 15 | 16 | 17 | 18 | 19 | 20 | 21 | |
| B-A (5 days) | 55.115 | 88.441 | 105.420 | 130.096 | 118.007 | 70.105 | 185.315 | 66.259 | 214.549 | 209.711 | |

TABLE 4

| | Aged (7.2 months or older) | | | | | | | | | | |
|---|---|---|---|---|---|---|---|---|---|---|---|
| | 1 | 2 | 3 | 4 | 5 | 6 | 7 | 8 | 9 | 10 | 11 |
| B-A (19 days) | 298.504 | 70.596 | 86.108 | 129.025 | 57.487 | 53.294 | 43.826 | 101.221 | 82.444 | 52.809 | — |
| | 12 | 13 | 14 | 15 | 16 | 17 | 18 | 19 | 20 | 21 | |
| B-A (19 days) | — | 131.569 | 88.695 | 61.725 | 27.070 | 32.708 | 22.406 | 20.515 | 59.409 | 136.814 | |

TABLE 5

| | Aged (7.2 months or older) | | | | | | | | | | |
|---|---|---|---|---|---|---|---|---|---|---|---|
| | 1 | 2 | 3 | 4 | 5 | 6 | 7 | 8 | 9 | 10 | 11 |
| B-A (33 days) | 114.33 | 148.154 | 21.599 | 71.410 | 4.797 | 24.240 | 11.079 | 42.621 | 31.969 | 23.509 | — |
| | 12 | 13 | 14 | 15 | 16 | 17 | 18 | 19 | 20 | 21 | |
| B-A (33 days) | — | 39.237 | 23.448 | 33.902 | 41.596 | 59.545 | 31.762 | 51.292 | 78.101 | 60.179 | |

As seen from Tables 1-5, the B–A value calculated from the β-amyloid concentration measurement 24 hours (1 day) after the administration of EPPS was positive (+) for all the mice, suggesting that the β-amyloid concentration in blood was increased after the administration of EPPS. Since the increase in the β-amyloid concentration in plasma after the administration of EPPS was confirmed in the β-amyloid aggregate forming mouse model using the kit according to the present disclosure, it can be seen that the diagnostic kit of the present disclosure can be used to diagnose or predict Alzheimer's disease, dementia, etc. more accurately.

Figure 3A:
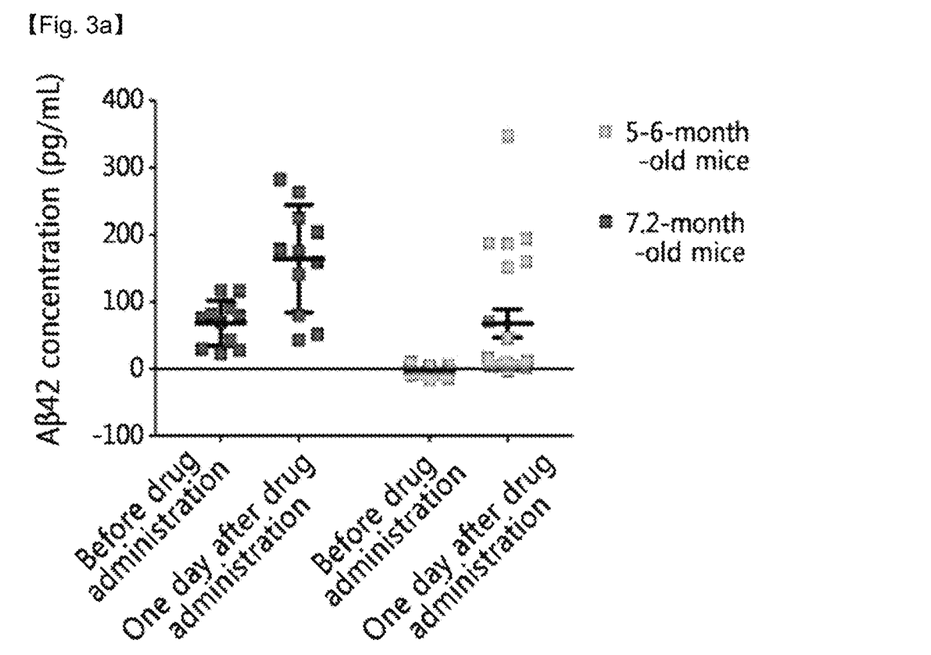
FIG. 3a shows the concentration of β-amyloid 42 in plasma before and 24 hours after administering a protein monomerizing composition according to an exemplary embodiment of the present disclosure.

As seen from FIG. 3a, significant increase in β-amyloid 42 concentration was observed after the administration of EPPS in 5-6-month-old (young) and 7.2-month-old (aged) mice.

Since 19 days after the administration of EPPS, the B–A value began to decrease, although there were differences depending on individuals. It is because, since the protein aggregates are cleared out of the brain by the drug after a predetermined time, the amount of the protein aggregates transported from the brain to the blood also decreases. Accordingly, the amount of the protein aggregates in blood which increases with time after the administration of EPPS decreases after a predetermined time, suggesting that the protein aggregates in the brain are decreased. Accordingly, the decrease in protein aggregates in the brain can be monitored through long-term drug administration and blood test.

Figure 3B:
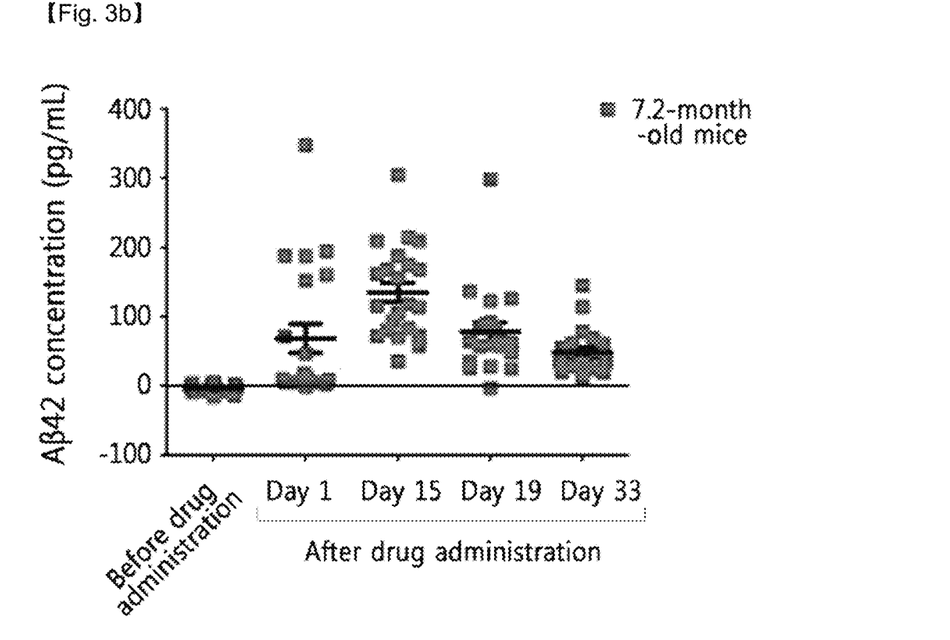
FIG. 3b shows the concentration of β-amyloid 42 in plasma before and 1 day, 5 days, 19 days and 33 days after administering a protein monomerizing composition according to an exemplary embodiment of the present disclosure.

As seen from FIG. 3b, 7.2-month-old (aged) mice showed significant increase in β-amyloid 42 concentration followed by decrease. That is to say, the dissociation of β-amyloid aggregates in the brain and the transportation to the blood could be observed with the diagnostic kit. In addition, the decrease in β-amyloid concentration in blood after a predetermined time was also observed. Accordingly, it can be seen that the blood diagnostic kit allows not only the diagnosis of diseases but also the monitoring of decrease in the protein aggregates in the brain.

<Example 2> Diagnostic Kit Measuring Dissociation Concentration of Aggregated Proteins in Blood Measurement of β-Amyloid Monomer Concentration and Diagnosis of Alzheimer's Disease Using APP/PS1/Tau Transgenic Mouse 1. Preparation of Mouse 5-month-old female APP/PS1/Tau transgenic mice were used as test animals.

The transgenic APP/PS1/Tau mouse model was B6;129-Psen1tm1MpmTg(APPSwe,tauP301L)1Lfa/Mmjax purchased from the Jackson Laboratory (USA) and maintained and used for experiments under the guideline of the Animal Care and Use Committee.

2. Treatment of Plasma and Whole Blood

Blood was collected in K2 EDTA-treated vacuum tube containing Roche Complete Mini (protease inhibitor) solution and centrifuged. Plasma separated from the cell fraction was collected in an Eppendorf tube and prepared into 0.1-mL samples, which were used immediately or stored at −80° C. for later use. Whole blood was collected in an Eppendorf tube by treating with EPPS and separating plasma from the cell fraction and prepared into 0.1-mL samples, which were used immediately for β-amyloid concentration measurement or stored at −80° C. for later use.

3. Sample Treatment and Measurement of β-Amyloid Concentration

The plasma was treated with water (control group) or EPPS (EPPS group).

As for the EPPS group, 15 μL of the plasma was treated with 5 μL of 400 mM EPPS, so that the final EPPS concentration was 100 mM. As for the control group, 15 μL of plasma was treated with 5 μL of PBS, so that the concentration was the same as that of the EPPS group. Each of the control group and the EPPS group was stirred at 4° C. for 24 hours.

The whole blood was analyzed after treating with EPPS.

15 μL of the whole blood was treated with 5 μL of 500 mM EPPS, so that the final EPPS concentration was 100 mM. After stirring at 4° C. for 24 hours, followed by centrifugation, plasma was collected for measurement of β-amyloid concentration.

The β-amyloid concentration in each plasma was measured using detection units 1 and 2 and MB/MP was calculated by a calculation unit using [Equation 2]. Average of three measurements is shown in Table 6.

Table 6 shows the monomer concentration of the plasma of the control group (UP Aβ), the plasma of the EPPS group (MP Aβ) and the whole blood of the EPPS group (MB Aβ), as well as UP/MP and MB/MP values.

TABLE 6

|  | UP Aβ | MP Aβ | MB Aβ | UP/MP | MB/MP |
|---|---|---|---|---|---|
| Concentration | 45.52 ± 17.10 | 49.53 ± 19.92 | 30.00 ± 5.32 | 0.92 | 0.61 |
| p value (paired t-test with MP) | 0.00675 | — | 0.00004 | — | — |

Figure 5:
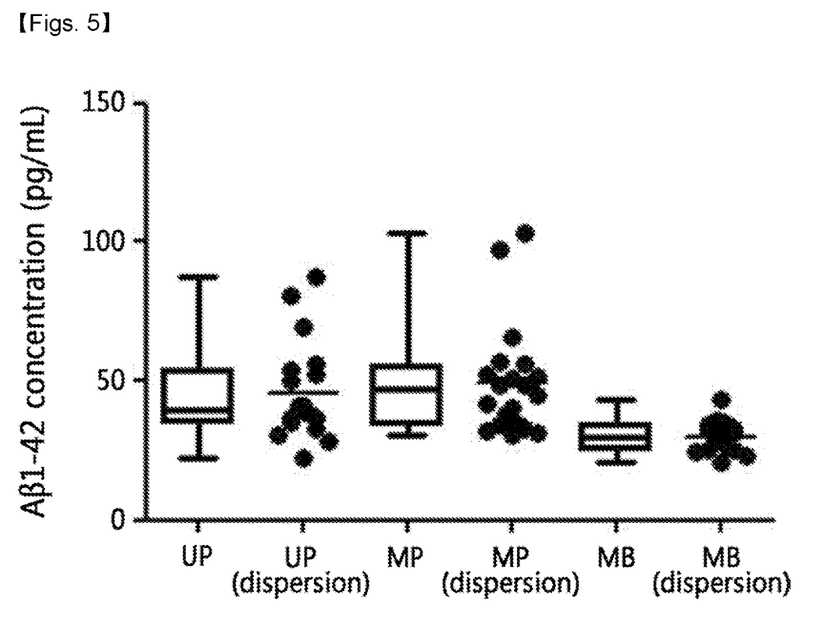
FIG. 5 shows the concentration of β-amyloid 42 in plasma or whole blood 24 hours after administering a protein monomerizing composition according to an exemplary embodiment of the present disclosure or PBS.

As seen from Table 6, since the monomer concentration in the plasma of the EPPS group (MP Aβ) was higher than that of the plasma of the control group (UP Aβ), it was confirmed that β-amyloids are dissociated into monomers by EPPS. The monomer concentration in the whole blood of the EPPS group (MB Aβ) was lower than UP Aβ (FIG. 5).

Also, since the UP/MP value calculated from the monomer concentration in the plasma of the control group (UP Aβ) and the EPPS group (MP Aβ) is smaller than 1.0 as 0.92 and the MB/MP value calculated from the monomer concentration in the plasma of the EPPS group (MP Aβ) and the monomer concentration in the whole blood of the EPPS group (MB Aβ) is smaller than 1.0 as 0.61, it may be diagnosed as a state wherein there is a risk of Alzheimer's disease or dementia is in progress. Since the decrease in the β-amyloid concentration in whole blood after the administration of EPPS was confirmed in the β-amyloid aggregate forming mouse model using the kit according to the present disclosure, it can be seen that the diagnostic kit of the present disclosure can be used to diagnose or predict Alzheimer's disease, dementia, etc. more accurately.

To give a further explanation of UP Aβ, MP Aβ and MB Aβ, UP Aβ stands for plasma containing β-amyloid in various forms (e.g., β-amyloid dimers, oligomers, profibrils, fibrils and plaques, β-amyloid 40/42 aggregates, β-amyloid monomers bound to other proteins, β-amyloid aggregates bound to other proteins, β-amyloid bound to fats, β-amyloid bound to carbohydrates, β-amyloid bound to nucleic acids and β-amyloid monomers bound to blood cells), MP Aβ stands for plasma containing β-amyloid which has been separated from UP Aβ and dissociated, and MB Aβ stands for plasma containing β-amyloid which has been separated after treating whole blood with EPPS. Accordingly, UP Aβ=[hetero Aβ], MP Aβ=[total Aβ monomers], and MP Aβ−MB Aβ=[aggregate Aβ].

<Example 3> Diagnostic Kit Measuring Dissociation Concentration of Aggregated Proteins in Blood Measurement of β-Amyloid Oligomer Concentration Using APP/PS1 Transgenic Mouse 1. Preparation of Mouse 9-month-old female APP/PS1 transgenic mice were used as test animals.

The transgenic APP/PS1 mouse model was B6C3-Tg (APPswe,PSEN1dE9)85Dbo/Mmjax purchased from the Jackson Laboratory (USA) and bred and used for experiments under the guideline of the Animal Care and Use Committee.

2. Treatment of Plasma and Whole Blood

Sample treatment and β-amyloid concentration measurement were conducted in the same manner as in Example 1.

Table 7 shows the monomer concentration of the plasma of the control group (UP Aβ), the plasma of the EPPS group (MP Aβ) and the whole blood of the EPPS group (MB Aβ), as well as UP/MP and MB/MP values. Average of three measurements is shown in Table 7.

TABLE 7

|  | UP Aβ | MP Aβ | MB Aβ | UP/MP | MB/MP |
|---|---|---|---|---|---|
| Concentration | 151.35 ± 20.35 | 151.58 ± 24.03 | 118.92 ± 10.22 | 0.99 | 0.79 |
| p value (paired t-test with MP) | 0.480 | — | 0.015 | — | — |

Figure 6:
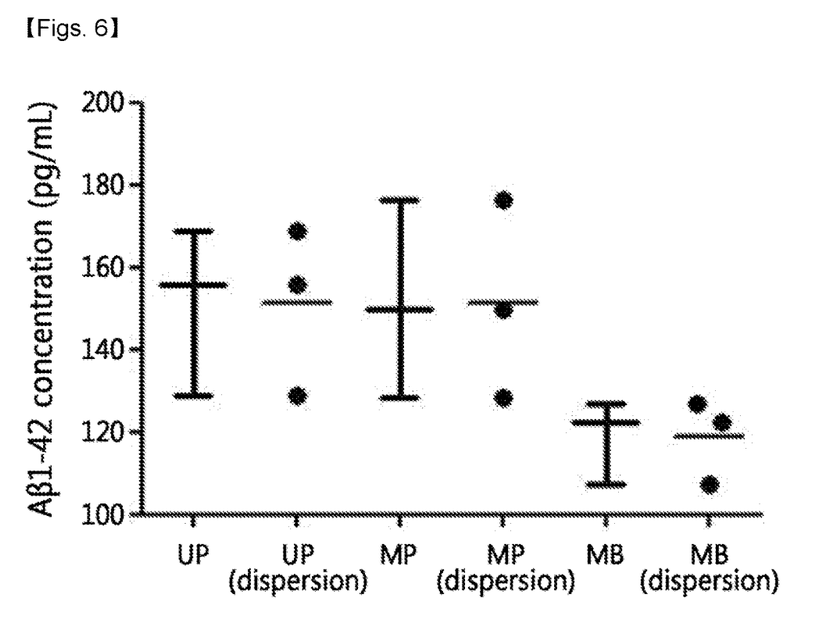
FIG. 6 shows the concentration of β-amyloid 42 in plasma or whole blood 24 hours after administering a protein monomerizing composition according to an exemplary embodiment of the present disclosure or PBS, measured using different mice from FIG. 5.

As seen from Table 7, the monomer concentration in the whole blood of the EPPS group (MB Aβ) was lower than UP Aβ (FIG. 6). Since the UP/MP value calculated from the monomer concentration in the plasma of the control group (UP Aβ) and the EPPS group (MP Aβ) is smaller than 1.0 as 0.99 and the MB/MP value calculated from the monomer concentration in the plasma of the EPPS group (MP Aβ) and the monomer concentration in the whole blood of the EPPS group (MB Aβ) is smaller than 1.0 as 0.79, it may be diagnosed as a state wherein there is a risk of Alzheimer's disease or dementia is in progress.

Since the decrease in the β-amyloid concentration in whole blood after the administration of EPPS was confirmed in the β-amyloid aggregate forming mouse model using the kit according to the present disclosure, it can be seen that the diagnostic kit of the present disclosure can be used to diagnose or predict Alzheimer's disease, dementia, etc. more accurately.

INDUSTRIAL APPLICABILITY

A diagnostic kit of the present disclosure may be used to diagnose diseases or disorders related with abnormal aggregation or misfolding of proteins.

The invention claimed is:
1. A diagnostic process for diagnosing diseases or disorders related with abnormal aggregation or misfolding of proteins, wherein said diseases or disorders related with abnormal aggregation or misfolding of proteins is Alzheimer's disease, comprising:
   measuring protein monomer concentration in plasma not treated with a protein monomerizing composition using detection unit 1';
   measuring protein monomer concentration in plasma treated with the protein monomerizing composition using detection unit 2';
   measuring protein monomer concentration in whole blood treated with the protein monomerizing composition using detection unit 3'; and
   calculating the ratio of the concentration measured by a detection unit 2' and the concentration measured by a detection unit 3' using [Equation 2] or calculating the ratio of the concentration measured by a detection unit 1' and the concentration measured by the detection unit 2' using [Equation 3]:

Protein monomer concentration in whole blood treated with protein monomerizing composition/Protein monomer concentration in plasma treated with protein monomerizing composition;    [Equation 2]

Protein monomer concentration in plasma not treated with protein monomerizing composition/Protein monomer concentration in plasma treated with protein monomerizing composition;    [Equation 3]

wherein said process diagnoses as Alzheimer's disease if the value calculated by the either equation 2 or equation 3 is smaller than 1.0; and
   wherein said protein monomerizing composition comprises 4-(2-Hydroxyethyl)-1-piperazinepropanesulfonic acid EPPS represented by [Chemical Formula 1] as an active ingredient

[Chemical Formula 1]

2. The diagnostic process for diagnosing diseases or disorders related with abnormal aggregation or misfolding of proteins according to claim 1, wherein the detection unit 1' measures the concentration of proteins in plasma separated from whole blood without treating with a monomerizing composition or 23-25 hours after treating with a phosphate-buffered saline (PBS) solution.

3. The diagnostic process for diagnosing diseases or disorders related with abnormal aggregation or misfolding of proteins according to claim 1, wherein the detection unit 2' and the detection unit 3' measure the concentration of proteins 23-25 hours after treating with the protein monomerizing composition.

4. The diagnostic process for diagnosing diseases or disorders related with abnormal aggregation or misfolding of proteins according to claim 1, wherein the monomerized protein is one that has been formed from dissociation of β-amyloid dimers, oligomers, profibrils, fibrils and plaques, β-amyloid 40/42 aggregates, β-amyloid monomers bound to other proteins, β-amyloid aggregates bound to other proteins, β-amyloid bound to fats, β-amyloid bound to carbohydrates, β-amyloid bound to nucleic acids and β-amyloid monomers bound to blood cells.

5. The diagnostic process for diagnosing diseases or disorders related with abnormal aggregation or misfolding of proteins according to claim 1, wherein the protein is β-amyloid.

* * * * *